United States Patent [19]

Austin et al.

US005631274A

[11] Patent Number: 5,631,274
[45] Date of Patent: May 20, 1997

[54] IMIDAZOLIUM, PYRAZOLIUM AND TRIAZOLIUM SALTS AS SWIMMING POOL SANITIZERS

[75] Inventors: Peter W. Austin, Bury; Clive H. Barlow, Heywood; Brian D. Bothwell, Castleton; Andrew N. Collins, Marsh; Mark R. James, Constable Lee Park, all of United Kingdom

[73] Assignee: Zeneca Limited, London, England

[21] Appl. No.: 411,633

[22] PCT Filed: Sep. 29, 1993

[86] PCT No.: PCT/GB93/02030

§ 371 Date: Apr. 11, 1995

§ 102(e) Date: Apr. 11, 1995

[87] PCT Pub. No.: WO94/08972

PCT Pub. Date: Apr. 28, 1994

[30] Foreign Application Priority Data

Oct. 20, 1992 [GB] United Kingdom .................. 9221997

[51] Int. Cl.$^6$ ............... C07D 233/58; C07D 233/56; A01N 43/50; A01N 43/56; A01N 43/653; C02F 1/150
[52] U.S. Cl. .................. 514/397; 210/167; 210/169; 210/749; 210/765; 548/266.6; 548/313.7; 548/314.4; 548/365.4; 514/383; 514/406
[58] Field of Search ................ 548/266.6, 313.7, 548/314.4, 365.4; 514/397, 383, 406; 210/167, 169, 749, 751, 765

[56] References Cited

U.S. PATENT DOCUMENTS

| 2,271,378 | 1/1942 | Searle ................... 548/314.4 X |
| 3,004,002 | 10/1961 | Kaplan et al. ............ 548/313.7 X |
| 3,853,907 | 12/1974 | Edwards .................. 548/313.7 |
| 3,855,235 | 12/1974 | McConnell ................ 548/313.7 |
| 4,684,736 | 8/1987 | Topel ..................... 548/313.7 |

FOREIGN PATENT DOCUMENTS

| 20077 | 12/1980 | European Pat. Off. ......... 548/313.7 |
| 239896 | 10/1987 | European Pat. Off. ......... 548/313.7 |
| 1747441 | 7/1992 | U.S.S.R. .................... 548/365.4 |
| 1355631 | 6/1974 | United Kingdom ............. 548/313.7 |
| 1503077 | 3/1978 | United Kingdom ............. 548/313.7 |

OTHER PUBLICATIONS

Chemical Abstracts, vol. 80, No. 6, Feb. 11, 1974, abstract No. 30718j "Antihelminthic preparation based on imidazole derivatives", p. 250, & FR,M,8 357 (Feb. 8, 1971).

Primary Examiner—Floyd D. Higel
Attorney, Agent, or Firm—Cushman Darby & Cushman IP Group Pillsbury Madison & Sutro LLP

[57] ABSTRACT

The use of oligomeric imidazolium, pyrazolium and triazolium salts as swimming pool sanitizers having improved compatibility with chlorine. Bisimidazolium salts are preformed.

19 Claims, No Drawings

IMIDAZOLIUM, PYRAZOLIUM AND TRIAZOLIUM SALTS AS SWIMMING POOL SANITIZERS

This application is a 371 of PCT/GB93/02030 filed Sep. 29, 1993.

The present invention relates to a method for inhibiting the growth of micro-organisms, especially bacteria and algae, in swimming pools and spas, particularly a method of treatment involving biologically active compounds which also exhibit some compatibility with chlorine, and to certain of the compounds themselves.

The water in swimming pools is constantly recirculated and fresh water is normally added only during the initial filling of the pool or during normal pool maintenance to maintain the desired volume. Although the water is filtered, usually continuously, to remove suspended matter, the water in the pool becomes contaminated by micro-organisms such as bacteria and algae and consequently requires the presence of biologically active compounds to inhibit this growth of micro-organisms for reasons of both hygiene and the aesthetic appearance of the water.

Although many different chemicals have been proposed as biologically active compounds in swimming pools in order to eliminate or inhibit the growth of micro-organisms, such chemicals must be carefully selected in order to provide protection from infection, ensure the health and comfort of bathers (e.g. taste, smell and feel of the water), compatibility with pool equipment (e.g. pumps) and compatibility with other pool chemicals.

It is conventional to add halogens to the water column, especially chlorine. This latter may be added as free chlorine, or more conveniently in the form of chlorine release compounds, such as isocyanurates. Isocyanurates, especially as alkaline earth salts, account for the largest usage of chlorine release compounds, particularly in the private swimming pool sector.

Major disadvantages of chlorine and chlorine release compounds are that they cause eye irritation and affect bathers with sensitive skin. Furthermore, for effective control of micro-organisms the level of chlorine in the water must be maintained at relatively high levels which requires regular additions of the chemicals to the water.

It is also conventional to inject ozonised air into the water to inhibit microbiological growth. Although ozone is an effective disinfectant, it is expensive and requires specialised dosing equipment and frequent additions to maintain the requisite minimum level of ozone. This method also suffers from the disadvantage that since high concentrations of ozonised air are injected into the pool at inlet ports, bathers having sensitive skin can be adversely affected and many bathers find the smell of ozone to be objectionable and it can cause headaches in certain individuals.

It has also been proposed in GB 1,407,258 to add a polymeric biguanide to the water of a pool to prevent or inhibit the growth of micro-organisms, especially bacteria and algae. At the levels of use required for effective disinfection, the biguanides do not cause skin irritation, even in bathers with sensitive skins. Furthermore, the biguanide is more persistent in the water and thus requires less frequent additions to maintain the desired level of protection than in the case of chlorine, chlorine release chemicals or ozonised air. Although acceptable to bathers, the biguanides may complex with certain metals to produce unpleasant and sticky gums which can adversely affect the filter of the swimming pool. Furthermore, during prolonged usage in a pool, certain algae can become resistent to the biguanide. It is, therefore, conventional to supplement the biguanide with hydrogen peroxide and/or quaternary ammonium compounds. However, hydrogen peroxide in concentrated form is corrosive and a potential fire hazard and requires careful handling and storage. Also, many quaternary ammonium compounds cause foaming which is objectionable in a swimming pool and can adversely affect the performance of the circulation pump. Furthermore, many quaternary ammonium compounds cause eye irritation and decompose to give objectionable fishy odours which are difficult to remove or produce a stable, clear, green colour in the water which is not aesthetically acceptable.

Thus, a swimming pool owner, especially in the privately-owned swimming pool sector, basically has the choice of maintaining his swimming pool with a chlorine release chemical or a polymeric biguanide. These two systems are not compatible or easily interchangeable. Thus, when a swimming pool which has been maintained on a polymeric biguanide for a lengthy period of time develops algae, although it is possible to remove the algae by addition of chlorine or chlorine release chemicals, re-conversion to the polymeric biguanide requires careful pre-treatment with reducing agents to remove the chlorine prior to re-establishing treatment with the polymeric biguanide. Conversely, if a pool, maintained on chlorine over a prolonged period of use, develops an algal bloom it is also possible to add the polymeric biguanide to combat the bloom although larger quantities of the biguanide are required due to loss by oxidation of the biguanide with the chlorine. Furthermore, re-establishing the pool on chlorine is more difficult and requires larger quantities of the chlorine release chemical due to the reducing capacity of the polymeric biguanide.

It is clearly an advantage for a swimming pool disinfectant to possess high activity against micro-organisms which develop in the water, a rapid rate of kill and persistence in use, freedom from foaming or formation of coloured complexes with dissolved metal salts and also sufficient compatibility with chlorine or chlorine release chemicals to allow economic dosing with chlorine and re-establishment of the biguanide. We have now found a class of heterocyclic salts which offer such advantages and exhibit improved compatibility with chlorine or chlorine-release chemicals. Such heterocyclic salts are oligomeric cationic imidazoles, pyrazoles and triazoles. Some dimeric cationic imidazolium salts derived from imidazole and 2-methylimidazole have been disclosed in UK 1,355,631 as antibacterials for use as antiseptics and disinfectants especially in pharmaceutical compositions. The alkyl and alkylene groups of such compounds contain even numbers of carbon atoms, and a wide variety of bridging groups are proposed which link the imidazolium rings together.

The hygiene requirements for bathing facilities with circulating water such as a swimming pool, a spa, a jacuzzi, a whirlpool, a recreational pond, a hot tub and the like are similar, and hereinafter such facilities will be referred to by the generic term "swimming pool".

According to the invention there is provided a method for inhibiting the growth of micro-organisms in a bathing facility which comprises adding to the water thereof from 1 to 1000 ppm of a heterocyclic salt of Formula (I)

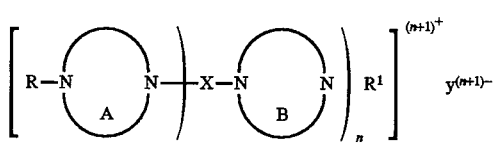

wherein

R and $R^1$ are independently $C_{1-24}$-hydrocarbyl or substituted $C_{1-24}$-hydrocarbyl;

A and B are independently a heterocyclic ring containing two or more nitrogen atoms;

X is $C_1$-$C_{20}$-alkylene;

n is 1 to 6; and

Y is one or more anions providing (n+1) negative charges to give a neutral molecule.

The groups R and $R^1$ are preferably the same and are preferably $C_{1-24}$-alkyl, more preferably $C_{4-20}$-alkyl, especially $C_{6-16}$-alkyl and more especially $C_{8-14}$-alkyl, and may be linear or branched.

When R and $R^1$ are substituted $C_{1-24}$-hydrocarbyl, the substituent is preferably halogen, especially chlorine or bromine, trifluormethyl, nitro or cyano.

X is preferably linear alkylene and especially $C_6$-$C_{18}$-alkylene, and more especially $C_{7-13}$-alkylene.

The anion Y may be polyvalent, but is preferably monovalent or divalent and more especially monovalent. When Y is divalent the number of anions required to form a neutral molecule will be ½(n+1), and when Y is trivalent the number of anions required to form a neutral molecule will be ⅓(n+1) and so on.

When Y is monovalent it may, for example, be alkylsulphate such as methosulphate; bicarbonate; bisulphate; acetate; and more especially halide, such as chloride, iodide and especially bromide. When Y is divalent it may, for example, be carbonate or sulphate. It is preferred that n is 1 or 2, and more especially that n is 1.

The heterocyclic salt may be added to the water of a swimming pool in an amount just sufficient to inhibit microbial growth but it is preferably added in larger amounts to allow for loss in use. The amount is preferably from 1 to 500 ppm, especially from 2 to 50 ppm and more especially from 5 to 25 ppm.

Although the pH of the water in the swimming pool containing the heterocyclic salt is not critical, it is preferably from 3 to 11 and especially from 5 to 9.

The heterocyclic rings A and B in the heterocyclic salt may be the same or different, but are preferably the same, and wherein at least one of the nitrogen atoms is a quaternary ammonium nitrogen atom. It is preferred that the heterocycle is a pyrazolium ring, a triazolium ring and especially an imidazolium ring.

When the heterocycle is an imidazolium ring, it is preferably of the Formula (II)

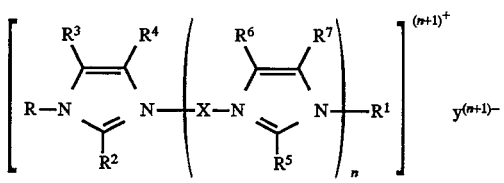

wherein R, $R^1$, X, Y and n are as hereinbefore defined; and $R^2$ to $R^7$ are each independently hydrogen or $C_{1-24}$-alkyl, or either both of the adjacent groups $R^3$ with $R^4$ and $R^6$ with $R^7$ together with the carbon atoms to which they are attached form a phenyl ring.

Preferably $R^2$ to $R^4$ are the same as $R^5$ to $R^7$ respectively. It is particularly preferred that at least one of $R^2$ to $R^4$ and $R^5$ to $R^7$ is alkyl and it is especially preferred that $R^3$, $R^4$, $R^6$ and $R^7$ are hydrogen and $R^2$ and $R^5$ are alkyl. When any one of $R^2$ to $R^7$ is alkyl it is preferably linear alkyl and more preferably $C_{1-10}$-alkyl and especially $C_{1-4}$-alkyl, such as methyl, ethyl or propyl.

When the heterocycle is a pyrazolium ring, it is preferably of the Formula (III)

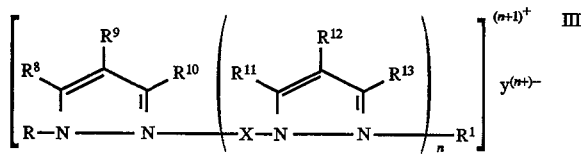

wherein R, $R^1$, X and n are as hereinbefore defined; and $R^8$ to $R^{13}$ are each independently hydrogen or $C_{1-24}$ alkyl; or any one or more of the adjacent pairs $R^8$ with $R^9$, $R^9$ with $R^{10}$, $R^{11}$ with $R^{12}$ and $R^{12}$ with $R^{13}$ together with the carbon atoms to which they are attached form a phenyl ring.

Preferably $R^8$ to $R^{10}$ are the same as $R^{11}$ to $R^{13}$ respectively. It is particularly preferred that each of $R^8$ to $R^{13}$ is either hydrogen or linear alkyl, especially $C_{1-10}$ alkyl and more especially $C_{1-4}$-alkyl, such as methyl, ethyl or propyl.

When the heterocycle is a 1,2,4-triazolium ring, it is preferably of the Formula (IV) or (V)

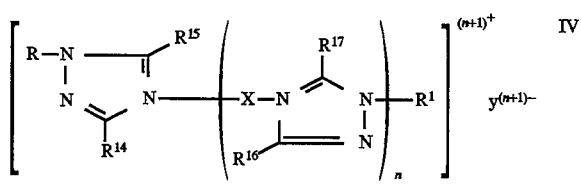

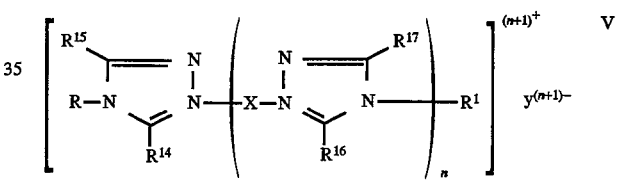

wherein

R, $R^1$, X, Y and n are as hereinbefore defined; and $R^{14}$ to $R^{17}$ are each independently hydrogen or $C_{1-20}$-alkyl.

It is preferred that $R^{14}$ is the same as $R^{17}$ and $R^{15}$ is the same as $R^{16}$. When $R^{14}$ to $R^{17}$ are alkyl they are preferably linear alkyl, especially $C_{1-10}$-alkyl and more especially $C_{1-4}$-alkyl, such as methyl, ethyl or propyl.

It will be appreciated that the compounds of general formulae II to V can exist in different tautomeric forms and all tautomeric forms thereof are included within the scope of the present invention.

The preferred heterocyclic salts for use as swimming pool disinfectants are the imidazolium salts of general formula II, particularly the dimers and trimers where n is 1 or 2 and especially the dimers where n is 1. We have also found that these di- and trimeric imidazolium salts exhibit superior persistence compared with the monomeric analogues (in which n=0) and also that those compounds containing an alkyl group attached to a carbon atom of the imidazolium ring, especially a 2-alkyl group, exhibit superior chlorine resistance compared with the imidazolium salts without such a substituent.

We have obtained useful effects with the following bis-imidazolium salts:

dodecyl-bis-(1-decyl-2-methylimidazolium)dibromide;
undecyl-bis-(1-decyl-2-methylimidazolium)dibromide;
decyl-bis-(1-undecyl-2-methylimidazolium)dibromide;

nonyl-bis-(1-decyl-2-methylimidazolium)dibromide;

nonyl-bis-(1-undecyl-2-methylimidazolium)dibromide;

dodecyl-bis-(1-nonyl-2-methylimidazolium)dibromide;

dodecyl-bis-(1-undecyl-2-methylimidazolium) dibromide;

undecyl-bis-(1-undecyl-2-methylimidazolium) dibromide;

dodecyl-bis-(1-decyl-2-ethylimidazolium)dibromide; and dodecyl-bis-(1-decyl-2,4,5-trimethylimidazolium) dibromide.

The first named compound has been found especially effective as a swimming pool disinfectant.

The compounds of general formula II are believed to be novel with the exception of decyl-bis-(1-decyl-2-methylimidazolium)dibromide. Thus, according to the invention there is provided a compound of Formula II with the exception of decyl-bis(1-decyl-2-methylimidazolium) dibromide.

According to a further feature of the invention there is provided the compound of Formula II wherein R and $R^1$ are both decyl; $R^3$, $R^4$, $R^6$ and $R^7$ are each hydrogen; $R^2$ and $R^3$ are each methyl; X is $C_{12}$ linear alkylene; n is 1 and Y is as hereinbefore defined. Preferably Y is chlorine or bromine, and especially bromine.

According to a further feature of the invention, there is provided a compound of general formula VI

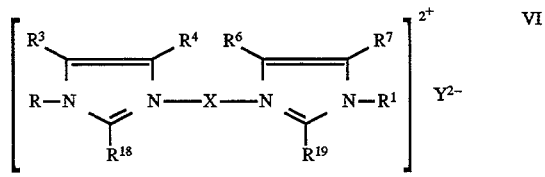

wherein $R^{18}$ and $R^{19}$ are independently $C_{1-4}$-alkyl; and

R, $R^1$, $R^3$, $R^4$, $R^6$, $R^7$, X and Y are as hereinbefore defined, provided that $R^{18}$ and $R^{19}$ are not both methyl.

Preferably $R^{18}$ and $R^{19}$ are $C_{2-4}$-alkyl.

An Example of compounds of Formula VI is dodecyl bis-(1-decyl-2-ethylimidazolium)dibromide.

According to a further feature of the invention there is provided a compound of Formula VII

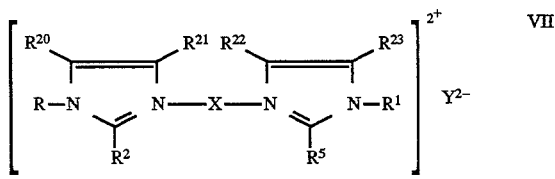

wherein $R^{20}$ to $R^{23}$ are each independently hydrogen or $C_{1-20}$-alkyl provided they are not all hydrogen; and R, $R^1$, $R^2$, $R^5$, X and Y are as hereinbefore defined.

When $R^{20}$ to $R^{23}$ are alkyl, they are preferably $C_{1-10}$-alkyl, and especially $C_{1-4}$-alkyl, such as methyl, ethyl and propyl.

An example of compounds of Formula VII is dodecyl bis(1-decyl-2,4(5)-dimethylimidazolium)dibromide mixed isomers.

According to a still further feature of the invention there is provided a compound of formula VIII

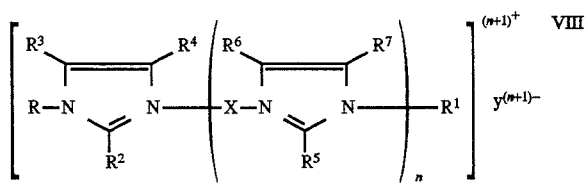

wherein

R to $R^7$, X and Y are all as hereinbefore defined; and n=2 to 6.

Preferably, n is 2 or 3.

Examples of compounds of formula VIII are bis(2-methyl-1-nonylimidazolium)-1,3-didecylene-2-methylimidazolium tribromide, bis-(1-decyl-2-methylimidazolium)-1,3-dihexylene-2-methylimidazolium tribomide and bis-(1-decyl-2-methylimidazolium)-1,3-didecylene-2-methylimidazolium tribromide.

Bis-imidazolium salts of general formulae VI and VII are typically prepared by heating an excess of a 1-alkylimidazole with a dihaloalkane at from 100° to 200° C. and preferably from 120° to 150° C. The reaction is preferably carried out neat without the presence of inert organic solvents. It is preferred that from 2 to 2.5 moles of 1-alkylimidazole is used for each mole of dihaloalkane. It is also preferred that the dihaloalkane is a dibromo compound so that the bis-imidazolium salt is isolated as the dibromide. Processes of this type are described in UK 1,355,631.

The tris-imidazolium salts of formula VIII are prepared in similar manner such as by reacting an imidazole of formula IX

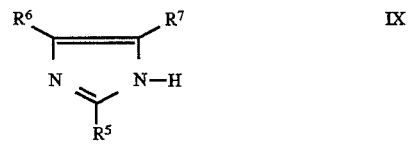

with excess dihalo-alkane, Hal-X-Hal, to obtain a 1,3-halo-di-substituted imidazolium salt of formula X

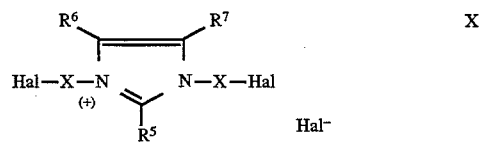

wherein $R^5$ to $R^7$ and X are all as hereinbefore defined, and Hal is halogen such as chlorine, iodine and especially bromine.

The reaction is preferably carried out neat; and the excess di-halo alkane acts as solvent. It is preferred to use at least 4 moles of dihaloalkane for each mole of imidazole. The reaction may be carried out at from 30° to 200° C., preferably from 40° to 100° C. for example 50° C. The compound of formula X is isolated by conventional means known to the art.

The tris imidazolium salt is prepared by reacting the compound of formula X with excess 1-substituted imidazole of formula XI

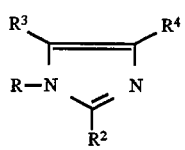

XI wherein R and $R^2$ to $R^4$ are all as hereinbefore defined. The reaction is preferably carried out under similar conditions for preparing the bis-imidazolium salts as previously described.

Certain of the above intermediates are new. Thus, as a still further feature of the invention there is provided a compound of formula X as hereinbefore described.

The reaction between the 1,3-dihalo substituted imidazolium salt of formula X or dihaloalkane, respectively, and the 1-substituted imidazole is typically carried out at temperatures from 30° to 200° C. The resulting bis or tris imidazolium salt generally separates from the reaction mass as a solid and can be isolated by conventional means.

The 1-substituted imidazoles used in the above processes can be made by any means known to the art and typically involves reacting a haloalkane with an imidazole in an inert solvent such as toluene in the presence of a base such as aqueous sodium hydroxide and a quaternary ammonium phase transfer catalyst. Such a process is described in Bull. Soc. Chem. Fr (1976) 1861.

The pyrazolium salts of Formula III are made in analogous manner by replacing the imidazole derivative with the equivalent pyrazole derivative.

The compounds of the present invention have antimicrobial properties. We have found that the compounds of formulae VI to VIII are active against a range of micro-organisms including algae, fungi, yeast and especially bacteria.

The compounds are particularly suitable for use as industrial biocides. They exhibit good wet state preservation especially in the presence of chlorine and hence may be used as a cutting fluid preservative and also in cooling water applications. They may also be used in paper mill liquors. Furthermore, the compounds may be used to preserve industrially important formulations, especially aqueous based formulations, which are used for coloration, such as dyestuffs and printing inks. They may also be used in the agrochemical industries to preserve formulations such as herbicide and pesticide flowables.

Still further important applications of the compounds of the present invention include their use in hydrocarbon fluids such as diesel fuels. They may also be incorporated into adhesives, cosmetics and personal care products in order to inhibit microbial spoilage.

The preservation of wood, leather and plastics materials is yet another important application of the compounds.

Especially important is the use of the compounds of general formula VI to VIII as a solid surface disinfectant and especially as a disinfectant for swimming pools as hereinbefore defined.

The compounds of formulae VI to VIII may be used alone as an antimicrobial material but may also be used in, or on, a suitable carrier material.

Thus, as a further aspect of the present invention there is provided a biocide composition comprising a carrier and an effective amount of a compound of general formulae VI to VIII.

The carrier is typically a material which shows little, if any, antimicrobial activity and may be, or include, a material which is susceptible to the growth of micro-organisms, especially bacteria. The carrier is preferably a liquid medium and the biocide composition may be a solution, suspension or emulsion of the compound of general formulae VI to VIII in a liquid carrier. The carrier is preferably water, which may contain water-misable solvents such as alcohols and glycols. When used as a swimming pool disinfectant the composition may also include a colourant which does not interact with the compound of formulae VI to VIII. Such colourants are preferably water soluble and are especially cationic in nature such as triphenylmethanes. The composition may also contain a fragrance.

The amount of the compound of formulae VI to VIII which is present in the biocide composition may be just sufficient to have an antimicrobial effect or the compound of formulae VI to VIII may be present in a substantially greater proportion. It will be appreciated that the biocide composition my be provided as a concentrated solution which is subsequently diluted for use as an antimicrobial material. The higher concentrations of the biocide composition are useful, for example, in the bulk transportation of the composition. Thus, the amount of the compound of formulae VI to VIII which is present in the biocide composition is typically in the range from 0.0001% up to 30% by weight of the biocide composition.

The compositions can be used for the treatment of various media to inhibit the growth of micro-organisms. The composition of the present invention is especially effective in providing anti-bacterial activity.

As a further aspect of the present invention there is provided a method for inhibiting the growth of micro-organisms on, or in, a medium which comprises treating the medium with a composition containing a compound of formulae VI to VIII as hereinbefore defined. The composition may contain only the compound of general formulae VI to VIII.

The compounds of formulae VI to VIII can be used in conditions in which micro-organisms grow and cause problems. Media in which micro-organisms cause problems include liquid, particularly aqueous, media such as cooling water liquors, paper mill liquors, metal working fluids, geological drilling lubricants, polymer emulsions and surface coating compositions such as paints, varnishes and lacquers and also solid materials such as wood and leather. The compounds of formulae VI to VIII can be included in such materials to provide an anti-microbial effect. Preferably, the compound of formulae VI to VIII is from 0.0001 up to 10%, preferably 0.0001 up to 5% and especially 0.0002 to 0.1% by weight relative to the media to which it is added. In many cases, microbial inhibition has been obtained with between 0.0005% and 0.01% by weight of the media.

The compounds of general formulae VI to VIII of the composition of the present invention may be the only antimicrobial compounds or may be used together with further compounds having antimicrobial characteristics. The composition may contain more than one compound of formulae VI to VIII. Alternatively, a composition of a compound of formulae VI to VIII in accordance with the present invention may be used together with one or more known antimicrobial compounds. The use of a mixture of anti-microbial compounds can provide a composition having a broader anti-microbial spectrum and hence one which is more generally effective than the components thereof. The known antimicrobial may be one possessing anti-bacterial, anti-fungal, anti-algal or other antimicrobial characteristic. The mixture of the compound of the present invention with other antimicrobial compounds typically contains from 1 to 99% by weight, and particularly from 40 to 60% by weight, relative to the weight of total antimicrobially active compounds, of the composition of a compound of formula VI to VIII.

Examples of known antimicrobial compounds which may be used with the compound of general formulae VI to VIII are quaternary ammonium compounds such as diethyldodecylbenzyl ammonium chloride; dimethyloctadecyl-(dimethylbenzyl)ammonium chloride; dimethyldidecylammonium chloride; dimethyldidodecylammonium chloride; trimethyl-tetradecylammonium chloride; benzyldimethyl ($C_{12}$–$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis(beta-hydroxyethyl)ammonium chloride; dodecylbenzyltrimethylammonium chloride; benzyldimethyl($C_{12}$–$C_{18}$ alkyl) ammonium chlforide; dodecyldimethylethyl ammonium ethylsulphate; dodecyldimethyl-(1-naphthylmethyl) ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivatives such as 1,3-bis(hydroxymethyl)-5,5-diemthylhydantoin; bis(hydroxymethyl)urea; tetrakis (hydroxymethyl)acetylene diurea; 1-(hydroxymethyl)-5,5-dimethylhydantoin and imidazolidinyl urea; amino compounds such as 1,3-bis(2-ethylhexyl)-5-methyl-5-aminohexahydropyrimidine; hexamethylene tetra amine; 1,3-bis(4-aminophenxoy)propane; and 2-[(hydroxymethyl)-amino]ethanol; imidazole derivatives such as 1[2-(2,4-dichlorophenyl)-2-(2-propenyloxy)ethyl]-1H-imidazole; 2-(methoxycarbonylamino)-benzimidazole; nitrile compounds such as 2-bromo-2-bromomethylglutaronitrile, 2-chloro-2-chloromethylglutaronitrile, 2,4,5,6-tetra- chloroisophthalodinitrile; thiocyanate derivatives such as methylene bis thiocyanate; tin compounds or complexes such as tributyltin-oxide, chloride, naphthoate, benzoate or 2-hydroxybenzoate; isothiazolin-3-ones such as 4,5-trimethylene-4-isothiazolin-3-one, 2-methyl-4,5-trimethylene-4-isothiazolin-3-one, 2-methylisothiazolin-3-one, 5-chloro-2-methylisothiazolin-3-one, benzisothiazolin-3-one, 2-methylbenzisothiazolin-3-one, 2-octylisothiazolin-3-one, thiazole derivatives such as 2-(thiocyanomethylthio)-benzthiazole; and mercaptobenzthiazole; nitro compounds such as tris(hydroxymethyl)nitromethane; 5-bromo-5-nitro-1,3-dioxane and 2-bromo-2-nitropropane-1,3-diol; iodine compounds such as iodo propynyl butyl carbamate and tri-iodo allyl alcohol; aldehydes and derivatives such as glutaraldehyde (pentanedial), p-chlorophenyl-3-iodopropargyl formaldehyde and glyoxal; amides such as chloracetamide; N,N-bis(hydroxymethyl)chloracetamide; N-hydroxymethyl-chloracetamide and dithio-2,2-bis (benzmethyl amide); guanidine derivatives such as poly hexamethylene biguanide nd 1,6-hexamethylene-bis[5-(4-chlorophenyl)biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichloro-phenoxy)phenol; thio-bis(4-chlorophenol) and 2-phenylphenol; sulphone derivatives such as diiodomethyl-paratolyl sulphone, 2,3,5,6-tetrachloro-4-(methylsulphonyl) pyridine and hexachlorodimethyl sulphone; thioamides such as dimethyldithiocarbamate and its metal complexes, ethylenebisdithiocarbamate and its metal complexes, and 2-mercaptopyridine-N-oxide and its metal complexes.

When used as a disinfectant for swimming pools, as hereinbefore defined, the compounds of formula I may be used together with other disinfectants and adjuvants commonly used in pools and spas. Such compounds include quaternary ammonium compounds such as those mentioned hereinbefore, biguanides such as poly(hexamethylenebiguanide), peroxy compounds such as hydrogen peroxide, copper salts and complexes such as copper sulphate, metal chelants such as ethylenediamine tetra-acetic acid, antifoam agents such as silicones, ozonized air, chlorine and chlorine release compounds such as calcium isocyanurate and inorganic salts used to balance the water or adjust the pH such as calcium chloride, sodium sulphate, sodium bisulphate, sodium bicarbonate and also chemicals which are commonly used to flocculate particulate matter from the water-column such as alum or ferrous-alum.

TEST PROTOCOLS (A) Primary Screen

A 0.2 ml volume of an 18-hour broth culture of *Escherichia coli* NCIB 9132 was added to 20 ml volumes of 10 ppm and 100 ppm test sanitizer in distilled water and in balanced water of 120 ppm alkalinity and 200 ppm calcium hardness to give an initial count of approximately $10^7$ viable cells/ml.

After contact times of 10 minutes and 3 hours a one-ml aliquot was removed and neutralised in 9 ml of 0.3% Azolectin- 2.0% Polysorbate 80.

Dilution counts are made using nutrient agar and survivors were enumerated after inoculation for 24 hours at 37° C.

(B) Compatibility with Chlorine

A sterile "balanced" water was prepared by dissolving $CaCl_2.2H_2O$ (30.7 parts) in a liter of distilled water and sterilizing at 121° C. for 20 minutes. 1 part by volume of this solution was added to 100 parts sterile distilled water to give 200 ppm calcium hardness. $NaHCO_3$ (19.7 parts) was dissolved in distilled water, filter sterilized and 1 part by volume was added to the solution containing 200 ppm calcium hardness to give 120 ppm alkalinity.

The test chemical was then added to 100 ml of the sterile "balanced" water to give a concentration of 10 ppm. Sodium dichloro-1,3,5-triazinetrione dihydrate (0.03 parts; Fichlor-Clearon) was then added to 10 ml distilled water and after standing for 15 minutes a 1 ml aliquot of the mixture was added to the test chemical in the "balanced" water to give a concentration of 30 ppm trione. This sample was stored in the dark for 3 days at 20°–25° C.

0.2 ml of a freshly prepared filter-sterilised solution containing 1% by weight of $Na_2S_2O_3.5H_2O$ was then added to the test mixture to give 100 ppm thiosulphate.

Finally, 0.2 ml of a 1 in 100 dilution of an 18 hour/30° C. broth culture of *E. coli* NCIB 9132 was transferred to 20 ml of the reaction mixture, and the number of surviving cells determined after contact times between 15 minutes and 3 hours.

(C) Rate of Kill in Deionised Water

One ml samples of the appropriate dilutions of sanitizers were added to 19 ml aliquots of sterile deionised water to give concentrations of 20, 10, 5 and 2.5 ppm of the sanitizer. A 0.2 ml volume of a 1 in 10 dilution in de-ionised water of an overnight (18 hours; 30° C.) shaken broth culture of *E.*

*coli* NCIB 9132 was transferred to each 20 ml volume of sanitizer solution. After contact periods of 0.5, 1, 3 and 5 minutes, 1 ml aliquots were removed from the test sample and added to 9 ml of 0.3% Azolectin/2% polysorbate neutraliser and the surviving cells were determined by the decimal dilution method on nutrient agar after incubation at 37° C. for 24 hours.

(D) Microtitre Screen

An overnight culture (18 hours; 37° C.) of *Escherichia coli* NCIB 9132 was prepared in nutrient broth and minimal medium respectively to give approximately $10^9$ viable cells per 1 ml of culture. 20 µl of the culture was then transferred aseptically to 20 ml of the appropriate medium. 200 µl of this inoculum was then added to all the first vertical wells of a microtitre plate and 100 µl inoculum added to each subsequent row of vertical wells.

A 5000 ppm solution of the chemical under test was prepared in an appropriate solvent, of which 20 µl was added to a well of the row of vertical wells to act as control. The contents of each well were mixed, 100 ml withdrawn and transferred to adjacent horizontal wells in that row. This process was repeated across each vertical row of wells to give a serial dilution of each compound under test ranging from 500 ppm to 0.25 ppm. The microtitre plate was then sealed and incubated at 37° C. for about 18 hours. The minimum inhibitory concentration (MIC) was indicated by the well with lowest concentration showing no turbidity.

The nutrient contained Lab-Lemco powder oxoid, Oxoid Bacteriological peptone L34 and sodium chloride in water.

The minimal medium consisted of an aqueous solution of disodium hydrogen orthophosphate, potassium dihydrogen orthophosphate, ammonium sulphate, ferrous sulphate, magnesium sulphate, calcium nitrate and glucose.

(E) Tank Recycling Test

One liter of balanced water (200 ppm calcium hardness, 120 ppm alkalinity adjusted to pH7.5 with sodium sulphate) containing 10 ppm test sanitiser in a polythene tank was recycled through 20 g sand at 4–5 hour turnover rate whilst maintaining a temperature of 20°–25° C.

The circulating water was inoculated daily (i.e. 5 times per week) with a suspension of *Pseudomonas fluorescens* NCIB 9046 in deionised water prepared from a 7 day/15° C. nutrient agar slant to give approximately $10^6$ cells/ml tank water.

Viable bacteria were determined three times a week (Monday, Wednesday, Friday) three hours after inoculation of *Ps. fluorescens*. If no survivors were detected, the sample was re-inoculated. If survivors ($>1 \times 10^3$/ml) were present a further 10 mg quantity of sanitiser was introduced in addition to the inoculum.

Throughout the experiment observations were made on the water clarity and appearance of turbidity.

At the end of the ten-week experimental period the viable counts of bacteria in the sand filter, and on the surface of the tank, and on the surface of plastic inserts in the tubing leading into and out of the tank were determined.

The invention is further illustrated by the following examples wherein all references are to parts by weight unless otherwise stated.

General Method for the Preparation of Bis-imidazolium Salts and Bis-pyrazolium Salts

EXAMPLE I (a) Preparation of 1-Decyl-2-methylimidazole

Ref: Henri 3.-M. Don and Jacques Metzger, Bull. Soc. Chim. Fr. (1976) 1861

A mixture of 2-methylimidazole (12.3 g; 0.15 mol), 1-bromodecane (33.15 g; 0.15 mol), sodium hydroxide solution (69.5 ml. of 11.5M solution; 0.8 mol) and tetra-n-butylammonium bromide (1.95 g; 0.006 mol) in toluene (300 ml) was stirred rapidly for 3 hours at 65° C. After cooling to between 20° and 25° C., the toluene layer was separated and extracted with 5M HCl solution (150 ml). The extract was neutralised with sodium bicarbonate and extracted many times into hexane. The hexane solution was dried over magnesium sulphate and evaporated to dryness to give an oil (25 g; 75% theory).

(b) Preparation of Dodecyl bis (1-decyl-2-methylimidazolium) dibromide

1-Decyl-2-methylimidazole (22.2 g; 0.1 mol) and 1,12-dibromododecane (16.4 g; 0.05 mol) were heated together at 120°–30° C. for 2 hours. The mixture was cooled to room temperature and the resultant viscous oil was stirred with ethyl acetate to give a white solid which was recrystallised from ethyl acetate/ethanol. Yield –25.9 g; 67% theory. M.pt. 114°–7° C.

This is referred to as Example 31 in the microbiological test data.

The 2-ethylimidazolium analogue is prepared in similar manner by replacing the 2-methylimidazole used in Example I with a molar equivalent of 2-ethylimidazole. This is referred to in the microbiological test data as Example 37. Similarly, by replacing the 2-methylimidazole used in Example I with 2,4-dimethylimidazole, the compound is obtained for which the biological test data is given as example 38. If the 2-methylimidazole used in Example I is replaced with the equivalent amount of 3,5-dimethylpyrazole, the bis-pyrazolium salt is obtained whose biological test data is given as example 40.

Homologous bis-imidazolium salts have also been prepared containing different numbers of carbon atoms as represented by R, $R^1$ and X in compounds of Formula II by replacing the 1-bromodecane and 1,12-dibromododecane used in Example I with the equivalent amount of the appropriate 1-bromoalkane or α,w-dibromoalkane. The biological text data for such compounds is given in Examples 1–30 and 32 to 36.

General Method for the Preparation of Tris-imidazolium Salts

EXAMPLE II (a) Preparation of 1-nonyl-2-methylimidazole

This was prepared by the process described in Example I but replacing the 1-bromodecane with an equivalent amount of 1-bromononane.

(b) Preparation of 1,3-dibromodecyl-2-methylimidazolium Bromide 2-methylimidazole (0.68 parts; 8.25 mole) and 1.10-dibromodecane (10.2 parts; 33 mmol; Aldrich) were stirred together at 50° C. for 5 hours. The reaction mass was then cooled, drowned into water (100 parts) and the reaction product extracted into dichloromethane. After washing the dichloromethane layer with water, the product was purified by column chromatography on silica gel, developed with dichloromethane (20 parts) containing methanol (1 part). After evaporating the solvent, the product was obtained as a white solid (0.9 parts, 18% theory yield).

Elemental analysis: Found 48.6% C, 7.4% H; 4.9% N Theory 47.9% C, 7.5% H; 4.7% N Proton NMR analysis in $CDC^{13}$ at 250 Hz: 3.4 (t), $Br-CH_2-$, 4H; 1.3(m), $-(CH_2)_7-$, 28H; 1.85(m), $-CH_2CH_2-N-$, 4H; 4.25(t), $-CH_2-CH_2-N-$, 4H; 2.8(s), $-N-C-CH_3$, 3H; 7.6(s), $-N-CH=$, 2H.

(c) Preparation of Bis(2-methyl-1-nonylimidazolium)-1,3-didecylene-2-methylimidazolium Tribromide Di-bromodecyl-2-methylimidazolium bromide (0.6 parts; 1.0 mmol; Example IIb) and 1-nonyl-2-methylimidazole (0.62 parts; 3.0 mmol; Example IIa) were heated with stirring at 50° C. for 6 hours. The reaction mass was then allowed to stand for 18 hours at 20°–25° C. The resultant clear viscous oil was triturated with ethylacetate and ether to give a soft white solid (0.9 parts, 88.5% theory yield).

Proton NMR analysis in $CDCl_3$ at 250 MHz: 0.9(t), $CH_3-C$, 6H; 1.3(m), $-CH_2-CH_2-CH_2-$, 48H; 1.8(m), $-N-CH_2-CH_2-$, 12H; 2.8(s), $-N-C-CH_3$, 9H; 4.3 (m), $-N-CH_2-CH_2-$, 12H; 7.5–7.75, $-N-CH=$, 6H.

This compound is referred to as Example 41 in the microbiological test data. Analogues have been prepared by replacing the 1-bromononane and 1,12-dibromododecane used in Example II with the equivalent amount of other 1-bromoalkanes and α,w-dibromoalkanes to obtain the compounds whose microbiological data is given as Examples 42 to 44.

EXAMPLE III

Preparation of the Imidazolium Tetramer Salt of Formula

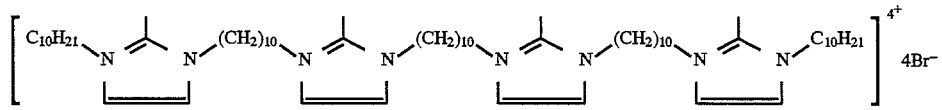

This compound is of general formula II wherein $R=R^1=C_{10}H_{21}$, $X=(CH_2)_{10}$, $R^2=R^5=CH_3$, $R^3=R^4=R^6=R^7=H$, n=3 and $Y=Br^-$ (a) Preparation of the Bis-imidazole of Formula

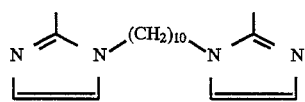

A two phase mixture of 2-methylimidazole (4.1 parts; 0.05 mol), 1,10-dibromodecane (7.5 parts; 0.025 mol) and tetra-N-butylammonium bromide (0.65 parts; 0.002 mol) in toluene (100 ml) and 11.5M sodium hydroxide solution (23 ml; 0.26 mol) was stirred rapidly at 65° C. for 4 hours. The cooled toluene layer was extracted with 5M hydrochloric acid (50 ml). The extract was washed with hexane, basified with sodium carbonate and extracted with ethylacetate. After washing with water and drying over magnesium sulphate the solvent was evaporated to give an oil (6.1 parts; 86% theory).

Proton NMR: δ($CDCl_3$); 1.25(m,12H); 1.7(m,4H); 2.35 (s,6H); 3.8(t,4H); 6.8(d,2H); 6.87(d,2H)ppm.

(b) Preparation of the Bis-imidazolium Salt of Formula

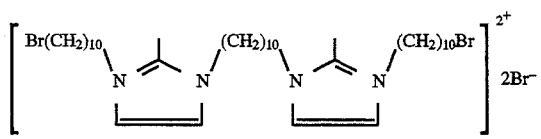

A solution of the bis-imidazole from (a) above (2.82 parts; 0.01 mol) and 1,10-dibromodecane (18 parts; 0.06 mol) in dimethylformamide (20 ml) was stirred at 50° C. for 3 hours. The mixture was diluted with water and excess dibromodecane was extracted into ethyl acetate. Potassium bromide (10 parts) was added to the water layer, and the product extracted into dichloromethane, dried over magnesium sulphate and evaporated to give an oil (5 parts; 55% theory).

Proton NMR δ($CDCl_3$): 1.25(m,40H); 1.75(m,8H); 2.75 (s,6H); 3.35(t,4H); 4.2(t,4H); 4.25(t,4H); 7.45(d,2H); 7.7(d, 2H)ppm.

Mass spec m/z(FAB): 819 $(M-Br)^+$; 739 $(819-HBr)^+$ (c) Title Compound

A mixture of the bis-imidazolium salt from (a) above (1.8 parts; 0.002 mol) and 1-decyl-2-methylimidazole (0.89 parts; 0.004 mol; ex Example Ia) was heated at 60° C. for 6 hours, allowed to stand over a weekend at room temperature, then heated at 125° C. for 1 hour. After cooling the mixture was stirred with ethyl acetate to remove residual starting materials leaving a viscous oil (2.2 parts; 81.6% theory).

Mass spec m/z(FAB): 1263(3Br); 1183(2Br); 1103(1Br).

General Method for the Preparation of Triazolium Salts

EXAMPLE IV

Preparation of the Bis-triazolium Salt of Formula

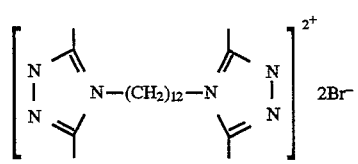

This is compound of general formula IV where $R=R^1=C_{10}H_{21}$, $R^{14}$ to $R^{17}=CH_3$, $X=(CH_2)_{12}$, n=1 and $Y=Br$.

(a) Preparation of N-acetamidoacetimidine

Ethyl acetimidate hydrochloride (2.47 parts; 20 mmol ex Aldrich) was added slowly to a solution of sodium hydroxide (0.8 parts; 20 mmol) in ethanol (50 ml). The precipitated sodium chloride was filtered and acetylhydrazine (1.48 parts; 20 mmol) was added to the filtrates. The solution was boiled for 10 minutes then cooled. The product was precipitated by addition of ether to give a white solid (0.6 parts; 26% theory). m.pt: 169°–173° C.

Elemental analysis: Found C, 41.7%; H, 8.3%; N, 36.8% $C_4H_9N_3O$ requires: C, 41.7%; H, 7.8%; N, 36.5%

Infra red analysis: $v_{max}$(nujol): 3376, 3187, 2921, 1294cm-1

(b) Preparation of 3,5-dimethyl-1,2,4-triazole

N'-Acetamidoacetimidine (0.29 parts; 2.5 mmol ex (a) above) was heated at 180° C. for 10 minutes. The resultant crystalline solid was recrystallised from a mixture of dichloromethane and 40–60 pet. ether to give a white solid (0.16 parts; 65% theory). m.pt: 140°–141° C.

Elemental analysis: Found C, 48.7%; H, 7.4%; N, 43.1% $C_4H_7N_3$ requires: C, 49.5%, H, 7.2%, N, 43.3%

Infra red analysis: $v_{max}$(nujol); 3179, 1591, 1305, 1063, 721, 701cm-1

(c) Preparation of 1-decyl-3,5-dimethyl-1,2,4-triazole

A mixture of 3,5-dimethyl-1,2,4-triazole (6.0 parts; 0.062 mol ex (b) above) and 1-bromodecane (14.4 parts; 0.065 mol) in dimethylformamide (16 ml) was heated together at 120° C. for 23 hours. The cooled reaction mixture was diluted with water (100 ml), a solution of sodium hydroxide (2.62 parts; 0.065 mol) in water (100 ml) added, and the product extracted into ether (3×50 ml). After drying over magnesium sulphate the solution was evaporated to yield a pale yellow oil (3.3 parts; 22% theory).

Infra red analysis: $v_{max}$(film): 2923, 2853, 1515, 1341, 701cm-1

Proton NMR: $\delta$(CDCl$_3$); 0.9(t,3H); 1.2–1.4(m,14H); 1.7–1.9(m,2H); 2.3(s,3H); 2.4(s,3H); 4.0(t,2H)ppm.

Mass spec: m/z(Br): 238(M+H$^+$, 100%)

(d) Title Compound

A mixture of 1-decyl-3,5-dimethyl-1,2,4-triazole (4.74 parts; 0.02 mol ex (c) above) and 1,12-dibromododecane (3.28 parts; 0.01 mol) was heated together at 120°–130° C. for 2 hours. The resulting oil was washed with ether then recrystallised from a mixture of ethyl acetate and ether to give a white solid (1.45 parts; 18% theory).

Elemental analysis: Found: C, 58.1%; H,9.6%; N, 9.9% $C_{40}H_{78}N_6Br_2$ requires C, 59.8%; H, 9.8%; N, 10.5%

Proton NMR: $\delta$(CDCl$_3$): 0.9(t,6H); 1.3–1.9(m,52H); 2.6(s,6H); 3.1(s,6H); 4.3(t,4H); 4.4(t,4H)ppm.

Mass spec: m/z(FAB): 721(M-Br)$^+$; 641(721-HBr)$^+$

EXAMPLE V

Preparation of the Bis-triazolium Salt of Formula

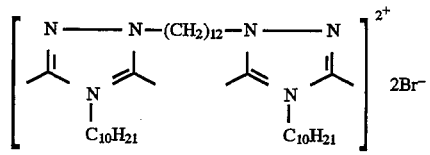

This is compound of general formula V where $R=R^1=C_{10}H_{21}$, $X=(CH_2)_{12}$, $R^{14}$ to $R^{17}=CH_3$, n=1 and $Y=Br^-$.

(a) Preparation of

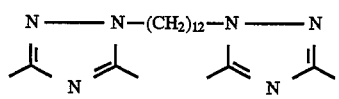

3,5-Dimethyl-1,2,4-triazole (5.63 parts; 0,058 mol ex IV(b) above), 1,12-dibromododecane (9.51 parts; 0,029 mol), tetra-N-butylammonium bromide (0.38 parts; 0.0012 mol) and 11.5M sodium hydroxide solution (13 ml) in toluene (60 mi) were stirred rapidly at 60°–70° C. overnight. After cooling the toluene layer was separated and extracted with 5M hydrochloric acid (30 ml). The extract was washed with hexane then was basified with 2M sodium hydroxide solution. The product was extracted into ethyl acetate, dried over magnesium sulphate and the solution evaporated to give an oil which crystallised on standing (7.64 parts; 73% theory).

Proton NMR: $\delta$(CDCl$_3$): 1.25(m,16H); 1.8(m,4H); 2.3(s, 6H); 2.4(s,6H); 3.95(t,4H)ppm Mass spec: m/z(EI): 360

(b) Title Compound

The bis-triazole from (a) above (3.6 parts; 0.01 mol) and 1-bromodecane (4.51 parts; 0.02 mol) were heated together at 120°–130° C. for 1.5 hours. The resultant viscous oil was washed with ethyl acetate then with ether to give a sticky solid (2.55 parts; 32% theory).

Elemental Analysis: Found C, 5.63%; H, 9.6%; N, 10.8% $C_{40}H_{78}N_6Br_2$ requires: C, 59.8%; H, 9.8%; N, 10.5%

Proton NMR: $\delta$(CDCl$_3$): 0.9(t,6H); 1.3, 1.75 and 1.9(m, 52H); 2.6(s,6H); 3.0(s,6H); 4.3(m,8H)ppm Mass spec: m/z(FAB): 721(M-Br)$_+$; 641(721-HBr)$^+$

MICROBIOLOGICAL TEST DATA

EXAMPLES 1 TO 36

Microbial Activity

The MIC values of a number of di-imidazolium dibromides were determined in both nutrient broth and in minimal medium using the method described in "Microtitre Screen." The compounds had the strucutre

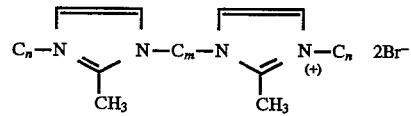

where n and m represent the number of saturated carbon atoms in the terminal alkyl group and linking alkylene group respectively. The results obtained are recorded in Table 1.

The compounds exhibiting the lowest MIC value are the most active microbiologically and those exhibiting the smallest change between nutrient broth and minimal medium indicate those compounds where the microbiological activity is least affected by organic matter and hence of greater potential as a swimming pool disinfectant.

As shown in Table 1, bis-imidazolium salts wherein n is from 8 to 14 and m is from 8 to 12 exhibit marked antimicrobial efficacy and those salts where n is from 9 to 11 and m is from 8 to 12 are little effected by organic matter. The compound wherein n is 10 and m is 12 is particularly useful since it exhibits similar activity in both nutrient broth and in minimal medium, thus indicating retention of activity in the presence of organic matter.

Compatibility with Chlorine

The compatibility of a number of di-imidazolium dibromides was determined using the test protcol "Compatibility with chlorine". The compounds had the chemical structure described in Examples 1 to 36 wherein both n and m are as previously indicated. The results are summarised in Table 2.

Those compounds where n is from 8 to 12 and m is from 7 to 12 exhibit good resistance to chlorine. Example 31 is supperior to Example 19 and examples 20 and 28 exhibit particularly good compatibility with chlorine.

TABLE 1

| Example | m | n | 8 | 9 | 10 | 11 | 12 | 14 | 16 | 20 | 22 |
|---------|---|---|---|---|----|----|----|----|----|----|----|
| 1 to 5 | 6 |   | >100 |   | 25 |   | 25 | >100 |   | >100 |   |
|        |   |   | >100 |   | 6 |   | 12 | 3 |   | 25 |   |
| 6 to 8 | 7 |   |   |   | 6 | 12 | 6 |   |   |   |   |
|        |   |   |   |   | 3 | 1.5 | 1.5 |   |   |   |   |
| 9 to 14 | 8 |   | >100 |   | 6 | 6 | 12 | >100 |   | >100 |   |
|         |   |   | >100 |   | 1.5 | 1.5 | 6 | 1.5 |   | 3 |   |
| 15 to 17 | 9 |   |   |   | 6 | 6 | 12 |   |   |   |   |
|          |   |   |   |   | 3 | 1.5 | 1.5 |   |   |   |   |
| 18 to 25 | 10 |   | 25 |   | 6 | 6 | 50 | >100 | >100 | >100 | >100 |
|          |   |   | 12 | 3 | 1.5 | 1.5 | 3 | 12 | 6 | 25 |   |
| 26 to 28 | 11 |   |   | 6 | 3 | 6 |   |   |   |   |   |
|          |   |   |   | 1.5 | 1.5 | 1.5 |   |   |   |   |   |
| 29 to 34 | 12 |   | 12 | 6 | 3 | 6 | >100 |   | >100 |   |   |
|          |   |   | 3 | 1.5 | 3 | 1.5 | 3 |   | 3 |   |   |
| 35 and 36 | 16 |   |   |   | 25 |   |   |   | >100 |   |   |
|           |   |   |   |   | 1.5 |   |   |   | 6 |   |   |

Footnote to Table 1
The upper value for each compound is the MIC in nutrient broth and the lower value is the MIC in minimal medium.
The example numbers in each horizontal column are numbered from the left of the table.

TABLE 2

| | | | Surviving cells after contact with chlorine for periods of | | | | | | |
|---|---|---|---|---|---|---|---|---|---|
| Example | n | m | 5 min | 15 min | 30 min | 45 min | 1 hr | 2 hr | 3 hr |
| 8 | 12 | 7 | >3.0E4 | 8.7E2 | <10 | <10 | <10 | <10 | <10 |
| 10 | 10 | 8 | >3.0E4 | 3.2E5 | >3.0E4 | >3.0E4 | 2.1E3 | <10 | <10 |
| 12 | 12 | 8 | 5.0E4 | 4.0E1 | <10 | <10 | <10 | <10 | <10 |
| 13 | 14 | 8 | >3.0E4 | 4.4E5 | 2.7E4 | 3.5E3 | 1.6E2 | <10 | <10 |
| 16 | 11 | 9 | >3.0E4 | 9.0E1 | <10 | <10 | <10 | <10 | <10 |
| 17 | 12 | 9 | 1.9E5 | 4.9E2 | <10 | <10 | <10 | <10 | <10 |
| 19 | 10 | 10 | >3.0E4 | 4.9E4 | 9.0E1 | <10 | <10 | <10 | <10 |
| 20 | 11 | 10 | 1.1E2 | <10 | <10 | <10 | <10 | <10 | <10 |
| 21 | 12 | 10 | 1.2E4 | 1.2E3 | <10 | <10 | <10 | <10 | <10 |
| 22 | 14 | 10 | >3.0E4 | >3.0E4 | >3.0E4 | >3.0E4 | >3.0E4 | >3.0E4 | >3.0E4 |
| 23 | 16 | 10 | >3.0E4 | >3.0E4 | >3.0E4 | >3.0E4 | >3.0E4 | 2.5E3 | 1.6E2 |
| 28 | 11 | 11 | 3.5E2 | <10 | <10 | <10 | <10 | <10 | <10 |
| 29 | 8 | 12 | >3.0E4 | 2.4E5 | >3.0E4 | >3.0E4 | 2.4E4 | <10 | <10 |
| 31 | 10 | 12 | 3.4E3 | 1.0E1 | <10 | <10 | <10 | <10 | <10 |
| 32 | 11 | 12 | 3.4E5 | 1.7E3 | <10 | <10 | <10 | <10 | <10 |
| 33 | 12 | 12 | 2.5E4 | 1.5E4 | 2.4E3 | 7.3E2 | 1.0E2 | <10 | <10 |
| 34 | 16 | 12 | >3.0E4 | >3.0E4 | >3.0E4 | >3.0E4 | >3.0E4 | 2.4E4 | 7.5E2 |
| 35 | 10 | 16 | >3.0E4 | >3.0E4 | >3.0E4 | >3.0E4 | 2.3E4 | 4.8E2 | 4.0E1 |

Footnote to Table 2
E is the logarithmic power to base 10 (e.g. 3.0E4 is $3 \times 10^4$ etc).
n and m are as referred to in Table 1.

Rate of Kill

The rate of kill of the following bis-imidazolium salts were determined by taking 0.2 ml aliquot of an overnight broth culture (18 hours, 37° C.) of *E. coli* NCIB 9517 in 20 mls of A.O.A.C. artificial hard water (200 ppm calcium hardness) containing 10 ppm of the test sanitizer. The initial cell count was approximately $10^5$ cells/ml, and after incubation at 37° C., the number of survivors were determined after contact periods from 0.5 minutes to 2 hours.

The compounds had the formula

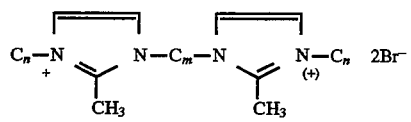

The results are summarised in Table 3 below.

Rate of Kill Versus *Escherichia coli* and *Enterococcus faecium*

The rate of kill for those sanitizers examined in Table 3 was determined against *Escherichia coli* 11229 (NCIB 9517) and *Enterococcus faecium* (ATCC 6569) using the AOAC Disinfectants for Swimming pool test.

The above strains were grown on Tryptone Soya Agar slants, and suspended, centrifuged and re-suspended in phosphate buffer dilution water, and 1 ml of the cell suspension was added to 199 ml of 10 ppm sanitiser solution in unbuffered freshly-distilled water.

The reaction mixture was maintained at 20° C., and after contact periods of 0.5, 1, 2, 3, 4, 5 and 10 min one-ml samples were transferred to neutraliser. Survivors were determined using Tryprone Soya Agar.

The results are summarised in Table 4 below.

TABLE 3

| Example | n | m | ½ min | 1 min | 3 min | 5 min | 10 min | 15 min | 30 min | 45 min | 1 hr | 1½ hr | 2 hr |
|---|---|---|---|---|---|---|---|---|---|---|---|---|---|
| A. DISTILLED WATER | | | | | | | | | | | | | |
| 10 | 10 | 8 | <10 | <10 | <10 | <10 | <10 | <10 | <10 | NT | NT | NT | NT |
| 19 | 10 | 10 | <10 | <10 | <10 | <10 | <10 | <10 | <10 | NT | NT | NT | NT |
| 29 | 8 | 12 | <10 | <10 | <10 | <10 | <10 | <10 | <10 | NT | NT | NT | NT |
| 31 | 10 | 12 | <10 | <10 | <10 | <10 | <10 | <10 | <10 | NT | NT | NT | NT |
| PHMB | | | 2.8E5 | 1.1E5 | 5.6E3 | 2.3E3 | 9.2E2 | 1.2E3 | 1.2E3 | 1.2E3 | 3.2E2 | 2.9E2 | 2.0E1 |
| B. 200 PPM CALCIUM HARDNESS (AOAC) WATER | | | | | | | | | | | | | |
| 10 | 10 | 8 | >3.0E5 | >3.0E5 | >3.0E5 | >3.0E5 | >3.0E5 | 2.2E5 | 1.5E5 | 4.7E3 | <10 | <10 | <10 |
| 19 | 10 | 10 | >3.0E5 | 1.4E5 | 6.7E3 | 1.6E2 | 1.0E1 | <10 | <10 | <10 | <10 | <10 | <10 |
| 29 | 8 | 12 | >3.0E5 | >3.0E5 | >3.0E5 | 1.3E3 | 6.7E2 | 1.7E2 | <10 | <10 | <10 | <10 | <10 |
| 31 | 10 | 12 | 1.4E3 | 2.0E1 | <10 | <10 | <10 | <10 | <10 | <10 | <10 | <10 | <10 |
| PHMB | | | 1.6E3 | 2.3E2 | <10 | <10 | <10 | <10 | <10 | <10 | <10 | <10 | <10 |
| C. 800 PPM CALCIUM HARDNESS (AOAC) WATER | | | | | | | | | | | | | |
| 10 | 10 | 8 | >3.0E5 | >3.0E5 | 1.9E5 | 2.4E5 | 3.5E5 | 1.9E5 | 2.6E5 | 2.1E5 | 1.6E5 | 1.3E5 | 6.2E4 |
| 19 | 10 | 10 | >3.0E5 | >3.0E5 | 3.4E5 | 1.6E5 | 1.4E5 | 1.4E5 | 4.7E4 | 5.4E3 | <10 | <10 | <10 |
| 29 | 8 | 12 | >3.0E5 | >3.0E5 | 4.8E5 | 3.7E5 | 3.2E5 | 2.2E5 | 1.8E5 | 2.4E5 | 1.5E5 | 1.1E5 | 6.9E4 |
| 31 | 10 | 12 | >3.0E5 | 4.3E5 | 9.4E4 | 1.3E5 | 4.1E4 | 2.0E4 | 1.4E3 | 1.0E1 | 2.0E1 | <10 | <10 |
| PHMB | | | >3.0E5 | 7.2E4 | 1.4E4 | 5.0E1 | <10 | <10 | <10 | <10 | <10 | <10 | <10 |
| Control | | | 4.8E5 | | | | | | | | | | |

Footnote to Table 3
m and n are as referred to in Table 1.

TABLE 4

| | | | Survivors (cells/ml) after Contact Periods of: | | | | | | |
|---|---|---|---|---|---|---|---|---|---|
| Example | m | n | ½ min | 1 min | 2 min | 3 min | 4 min | 5 min | 10 min |
| A) *Enterococcus faecium* ATCC 6569 | | | | | | | | | |
| 10 | 10 | 8 | 8.3E6 | 6.6E5 | 5.9E4 | 5.4E2 | 6.0E1 | 2.0E1 | <10 |
| 19 | 10 | 10 | 3.5E4 | 1.6E2 | 3.0E1 | <10 | <10 | <10 | <10 |
| 29 | 8 | 12 | 5.3E5 | 7.7E4 | 4.3E4 | 7.4E3 | 1.2E2 | 3.0E1 | <10 |
| 31 | 10 | 12 | 3.0E1 | <10 | <10 | <10 | <10 | <10 | <10 |
| PHMB | | | 1.2E7 | 1.1E7 | 3.8E6 | 6.8E6 | 6.4E6 | 3.9E6 | 2.8E6 |
| Control | | | 4.4E7 | | | | | | |
| B) *Escherichia coli* ATCC 11229 | | | | | | | | | |
| 10 | 10 | 8 | 1.9E3 | 2.1E2 | 4.7E2 | 2.4E2 | 1.3E2 | 1.1E2 | 3.0E1 |
| 19 | 10 | 10 | 2.0E1 | <10 | <10 | <10 | <10 | <10 | <10 |

TABLE 4-continued

| Example | m | n | ½ min | 1 min | 2 min | 3 min | 4 min | 5 min | 10 min |
|---|---|---|---|---|---|---|---|---|---|
| 29 | 8 | 12 | 3.1E2 | <10 | <10 | <10 | <10 | <10 | <10 |
| 31 | 10 | 12 | <10 | <10 | <10 | <10 | <10 | 2.0E1 | <10 |
| PHMB | | | 7.9E5 | 4.6E5 | 2.3E5 | 2.0E5 | 1.1E5 | 9.9E5 | 2.8E4 |
| Control | | | 1.6E6 | | | | | | |

The time required to give a log 5 kill against the two organisms listed in Table 4 using the A.O.A.C. Disinfectants test for swimming pools was determined and the results are summarised in Table 5 below.

TABLE 5

| | | | Time (min) for 10 ppm to give a 5 log kill against | |
|---|---|---|---|---|
| Example | n | m | Enterococcus faecium | Escherichia coli |
| 10 | 10 | 8 | 4 | >10 |
| 19 | 10 | 10 | 1 | 1 |
| 29 | 8 | 12 | 4 | 1 |
| 31 | 10 | 12 | 0.5 | 0.5 |
| PHMB | | | >10 | >10 |

Footnote to Tables 4 & 5
m and n are as referred to in Table 1.
Effect of a alkyl substitutent in the imidazolium ring on chlorine compatibility of bis-imidazolium salts The chlorine compatibility of the following compounds was determined using a variant on the "Compatibility with chlorine" protocol except that 0.01 parts sodium-1,3,5-triazinetrione were used, and the contact time was increased to 24 hours.

The compounds had the following structure, and the results are given in Table 6 below.

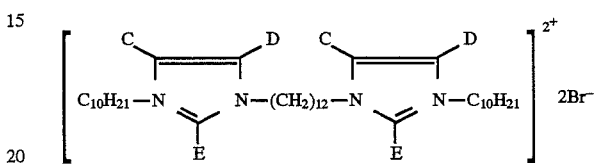

The compound referred to in example 37 exhibits higher activity than the 2-methylimidazolium anaologue and has an MIC in nutrient broth of 1.56 ppm and 0.8 ppm in minimal medium.

The compound where C, D and E are all hydrogen exhibits poor chlorine compatibility compared with the compounds where E is neither methyl or ethyl.

TABLE 6

| Example | C | D | E | Chlorine Variant | Survivors (cells/ml) after | | | | | | | |
|---|---|---|---|---|---|---|---|---|---|---|---|---|
| | | | | | 2 min | 5 min | 10 min | 15 min | 20 min | 30 min | 1 hr | 2 hr |
| 31 | H | H | Me | − | <10 | <10 | <10 | NT | NT | NT | NT | <10 |
| | | | | + | NT | 1.3E3 | 2.0E1 | <10 | <10 | <10 | <10 | <10 |
| 37 | H | H | Et | − | <10 | <10 | <10 | NT | NT | NT | NT | <10 |
| | | | | + | NT | 3.5E4 | 3.6E4 | 3.3E4 | 9.4E3 | 3.3E2 | <10 | <10 |
| 38 | Me | | Me* | − | <10 | <10 | <10 | NT | NT | NT | NT | <10 |
| | | | | + | NT | 4.9E3 | 2.0E1 | <10 | <10 | <10 | <10 | <10 |
| 39 | H | H | H | − | 3.0E1 | <10 | <10 | NT | NT | NT | NT | <10 |
| | | | | + | NT | 4.3E5 | 3.0E4 | >3.0E4 | >3.0E4 | >3.0E4 | >3.0E4 | >3.0E4 |
| Control | | | | | 5.3E5 | | | | | | | |

Footnote to Table 6
*this is a mixed imidazolium salt obtained from 2,4-dimethylimidazole.

Further Examples of Bisimidazolium Salts and Bis-pyrazolium Salts

The following compounds listed in Tables 7A and 7B were evaluated for resistance to chlorine using the "Chlorine Compatibility" protocol and also for biocidal activity against E coli in the presence of hard water using the "Primary Screen" protocol. The results are summarised in Table 7A and 7B respectively.

The results indicate that the presence of a phenyl ring as a bridging group in bisimidazolium salts adversely affects chlorine tolerance, and that bispyrazolium salts also exhibit some chlorine compatibility.

TABLE 7A

| Example or Comp | Survivors (cells/ml) after contact period of: | | | | |
|---|---|---|---|---|---|
| | No Chlorine | | Presence of Chlorine | | |
| Example | 15 min | 3 hr | 15 min | 3 hr | 24 hr |
| 10 | >3.0E5 | <10 | >3.0E5 | <10 | <10 |
| 12 | <10 | <10 | 6.1E3 | <10 | <10 |
| 29 | >3.0E5 | <10 | >3.0E5 | <10 | <10 |
| 40 | 8.1E4 | <10 | 2.8E5 | 8.1E4 | <10 |
| A | 2.1E3 | <10 | >3.0E5 | 4.9E2 | <10 |
| PHMB | <10 | <10 | >3.0E5 | >3.0E4 | >3.0E4 |
| Control | 4.9E6 | | 3.7E6 | | |

TABLE 7B

| | Primary Screen | | | | | |
|---|---|---|---|---|---|---|
| | Distilled Water | | 200 ppm hard water | | 800 ppm Calcium hardness | |
| Example | 10 min | 3 hr | 10 min | 3 hr | 10 min | 3 hr |
| 10 | <10 | <10 | 1.8E6 | <10 | 1.5E5 | <10 |
| 12 | 5.0E1 | 3.0E1 | 6.0E1 | <10 | <10 | <10 |
| 29 | <10 | <10 | >3.0E5 | <10 | 1.7E5 | <10 |
| 40 | <10 | <10 | >3.0E5 | <10 | 1.3E5 | 1.7E2 |
| A | <10 | <10 | 1.6E6 | <10 | 1.7E5 | <10 |
| PHMB | <10 | <10 | <10 | <10 | <10 | <10 |

Footnote to Tables 7A and 7B
Example 40 is decyl bis-(N-decyl-3,5-dimethylpyrazolium)dibromide
Example A is 1,4-xylyl bis (N-dodecyl-2-methylimidazolium)dibromide

Tank Recycling Test

The compounds listed in Table 8 below were compared in the tank recycling test as outlined in the Test protocols. The results are summarised in Table 8 below.

The bis-imidazolium salt (Example 19) required less than half the number of additions of sanitizer to inhibit microbial growth compared with the analogous bis-pyrazolium salt (Example 37) and the monomeric equivalent mono-imidazolium salt (Comparative Example B).

TABLE 8

| | Number of Additions of Sanitizer required to control microbial growth by week | | | | | | | | | |
|---|---|---|---|---|---|---|---|---|---|---|
| Example | 1 | 2 | 3 | 4 | 5 | 6 | 7 | 8 | 9 | 10 |
| 19 | 1 | 1 | 1 | 1 | 1 | 1 | 1 | 1 | 2 | 3 |
| 40 | 2 | 3 | 3 | 3 | 5 | 5 | 6 | 7 | 7 | 7 |
| B | 1 | 1 | 2 | 3 | 3 | 4 | 4 | 5 | 7 | 7 |

Footnote to Table 8
B is 1,3-didecyl-2-methylimidazolium bromide.

Bisimidazolium Salts Having an Odd Number of Carbon Atoms in the Alkyl/alkylene Chains The rates of kill for the compounds listed in Table 9 below were determined using the Rate of Kill method described hereinbefore in the protocol. Examples 30, 11, 16 and 27 are particularly effective in exhibiting a log 5 kill within 1 minute at a concentration of 20 ppm.

These compounds were also evaluated for chlorine resistance as described in the protocol "Compatibility with Chlorine". The results are summarised in Table 10 below, and all the compounds exhibit significant retention of activity after contact with chlorine. They also exhibit high activity both in the presence and absence of organic matter as summarised in Table 1.

TABLE 9

| Example | Conc (ppm) | Survivors (cells/ml) after contact periods of | | |
|---|---|---|---|---|
| | | 1 min | 3 min | 5 min |
| 6 | 20 | 8.1E2 | <10 | <10 |
| | 10 | >3.0E4 | 2.1E4 | 1.3E2 |
| | 5 | >3.0E4 | >3.0E4 | >3.0E4 |
| | 2.5 | >3.0E4 | >3.0E4 | >3.0E4 |
| 11 | 20 | <10 | <10 | <10 |
| | 10 | 1.6E2 | <10 | <10 |
| | 5 | 1.1E4 | 7.0E1 | <10 |
| | 2.5 | >3.0E4 | 8.7E3 | 7.0E2 |
| 15 | 20 | <10 | <10 | <10 |
| | 10 | 1.5E4 | <10 | <10 |
| | 5 | >3.0E4 | 6.0E4 | 7.4E3 |
| | 2.5 | >3.0E4 | >3.0E4 | >3.0E4 |
| 16 | 20 | <10 | <10 | <10 |
| | 10 | 3.4E2 | <10 | <10 |
| | 5 | 1.7E3 | 2.1E2 | <10 |
| | 2.5 | 5.6E4 | 9.7E3 | 4.1E3 |
| 21 | 20 | <10 | <10 | <10 |
| | 10 | 2.1E3 | <10 | <10 |
| | 5 | 3.9E4 | 6.4E3 | 3.1E2 |
| | 2.5 | <3.0E4 | 8.7E4 | 3.7E4 |
| 27 | 20 | <10 | <10 | <10 |
| | 10 | 7.0E2 | <10 | <10 |
| | 5 | 9.7E3 | 2.9E2 | <10 |
| | 2.5 | 3.7E4 | 1.1E4 | 9.6E2 |
| 30 | 20 | <10 | <10 | <10 |
| | 10 | 1.1E2 | <10 | <10 |
| | 5 | 5.2E3 | <10 | <10 |
| | 2.5 | 4.1E4 | 5.4E3 | 7.9E2 |
| PHMB | 20 | >3.0E4 | >3.0E4 | >3.0E4 |
| | 10 | >3.0E4 | >3.0E4 | >3.0E4 |
| | 5 | >3.0E4 | >3.0E4 | >3.0E4 |
| | 2.5 | >3.0E4 | >3.0E4 | >3.034 |
| Control | | 8.6E7 | | |

TABLE 10

| Example | Survivors (cells/ml) after contact period of: | | | |
|---|---|---|---|---|
| | (No chlorine) | | (Presence of Chlorine) | |
| | 15 min | 3 hr | 15 min | 3 hr |
| 6 | >3.0E5 | <10 | >3.0E4 | <10 |
| 11 | 2.2E2 | <10 | 4.3E4 | <10 |
| 15 | >3.0E5 | <10 | >3.0E3 | <10 |
| 16 | 3.0E1 | <10 | 1.1E4 | <10 |
| 26 | >3.0E5 | <10 | >3.0E5 | <10 |
| 27 | >3.0E5 | <10 | >3.0E5 | <10 |
| 30 | >3.0E5 | <10 | >3.0E4 | <10 |
| PHMB | 7.3E2 | <10 | >3.0E5 | >3.0E5 |

All the above disinfectants having an odd number of carbons in the alkyl or alkylene linking group retained significant activity after contact with chlorine.

Tris-imidazolium Salts

A number of tris-imidazolium salts have been prepared by the method described in Example II and evaluated as swimming pool disinfectants. They have the following general formula

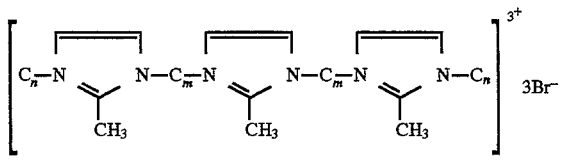

wherein n and m represent saturated alkyl and alkylene chains respectively.

Their microbiocidal activity was determined by the Primary Screen protocol and their chlorine compatability and efficacy in the tank test was also determined using the appropriate test protocol. The results are summarised below in Tables 11A, 11B and 11C.

TABLE 11A

PRIMARY SCREEN

| | | | Survivors (cells/ml) after | |
|---|---|---|---|---|
| Example | n | m | 10 min | 3 hr |
| 41 | 9 | 10 | >3.0E4 | 1.0E1 |
| 42 | 10 | 6 | >3.0E4 | >3.0E4 |
| 42 | 8 | 6 | >3.0E4 | >3.0E4 |
| 44 | 10 | 10 | >3.0E5 | <10 |
| PHMB | | | >3.0E4 | 2.0E1 |

TABLE 11B

CHLORINE COMPATABILITY

| | | | Survivors (cells/ml) | | | |
|---|---|---|---|---|---|---|
| | | | No Chlorine | | After contact with chlorine | |
| Example | n | m | 10 min | 3 hr | 10 min | 3 hr |
| 41 | 9 | 10 | 6.3E3 | <10 | 5.8E3 | <10 |
| 45 | 16 | 16 | 1.0E2 | <10 | >3.0E5 | >3.0E4 |
| PHMB | | | <10 | <10 | >3.0E5 | >3.0E5 |
| Control | | | 5.3E5 | | 8.2E5 | >3.0E4 |

TABLE 11C

TANK TEST

| | Number of additions of chemicals required to control microbial growth by week | | | | | | | | |
|---|---|---|---|---|---|---|---|---|---|
| Example | 1 | 2 | 3 | 4 | 5 | 6 | 7 | 8 | 9 |
| 41 | 1 | 1 | 1 | 1 | 1 | 1 | 1 | 1 | 1 |
| PHMB | 1 | 1 | 1 | 1 | 1 | 1 | 2 | 2 | 2 |

We claim:

1. A method for inhibiting the growth of micro-organisms in a bathing facility which comprises adding to the water thereof from 1 to 1000 ppm of a heterocyclic salt of the formula I

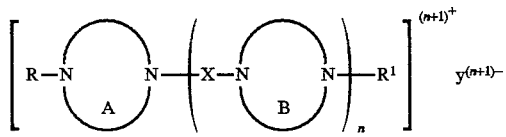

wherein

R and $R^1$ are independently $C_{4-20}$-alkyl;

A and B are independently a pyrazolium, triazolium or imidazolium ring;

X is $C_{6-18}$-alkylene;

n is 1 to 6; and

Y is one or more anions providing (n+1) negative charges to give a neutral molecule.

2. A method as claimed in claim 1 wherein R and $R^1$ are the same.

3. A method as claimed in claim 1 or wherein R and $R^1$ is $C_{8-14}$ alkyl.

4. A method as claimed in claim 1 wherein X is $C_{7-13}$ alkylene.

5. A method as in claim 1 wherein n is 1 or 2.

6. A method as claimed in claim 1 wherein the heterocyclic salt has the Formula II

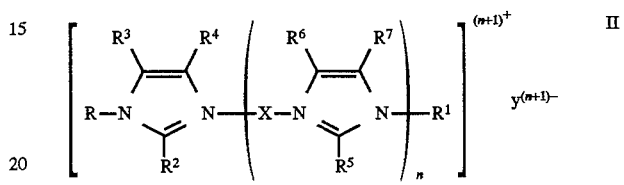

wherein

R, $R^1$, X, Y and n are as defined in claim 1; and $R^2$ to $R^7$ are each independently hydrogen or $C_{1-4}$-alkyl or either both of the adjacent groups $R^3$ with $R^4$ and $R^6$ with $R^7$ together with the carbon atoms to which they are attached form a phenyl ring.

7. A method as claimed in claim 6 wherein $R^3$, $R^4$, $R^6$ and $R^7$ are all hydrogen and $R^2$ and $R^5$ are $C_{1-4}$-lower alkyl.

8. A method as claimed in claim 1 wherein the heterocyclic salt has the Formula III

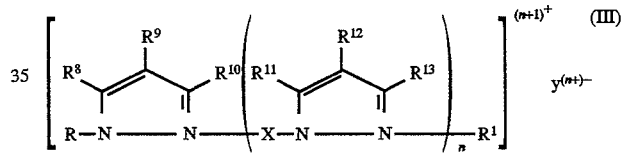

wherein

R, $R^1$, X, Y and n are as defined in claim 1; and $R^8$ to $R^{13}$ are independently hydrogen or $C_{1-24}$-alkyl; or any one or more adjacent pairs $R^8$ with $R^9$, $R^9$ with $R^{10}$, $R^{11}$ with $R^{12}$ or $R^{12}$ with $R^{13}$ together with the carbon atoms to which they are attached form a phenyl ring.

9. A method as claimed in claim 1 wherein the heterocyclic salt has the Formula IV or V

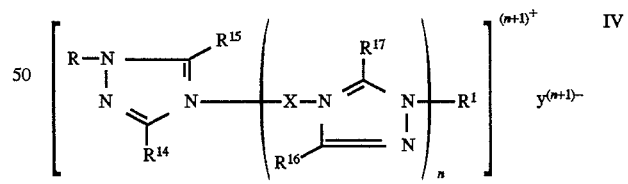

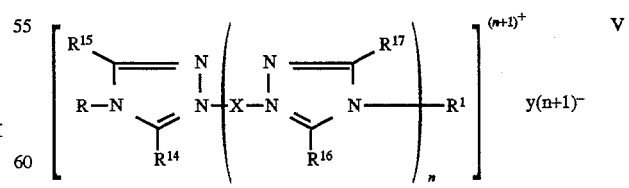

wherein

R, $R^1$, X, Y and n are as defined in claim 1; and $R^{14}$ to $R^{17}$ are independently hydrogen or $C_{1-4}$-alkyl.

10. A method as claimed in claim 6 wherein the hetrocyclic salt is selected from dodecyl bis-(1-decyl-2-methylimidazolium)dibromide;

undecyl-bis-(1-decyl-2-methylimidazolium)dibromide;
decyl-bis-(1-undecyl-2-methylimidazolium)dibromide;
nonyl-bis-(1-undecyl-2-methylimidazolium)dibromide;
nonyl-bis(1-decyl-2-methylimidazolium)dibromide;
dodecyl-bis-(1-nonyl-2-methylimidazolium)dibromide;
dodecyl-bis(1-undecyi-2-methylimidazolium)dibromide;
undecyl-bis(1-undecyl-2-methylimidazolium)dibromide:
dodecyl-bis(1-decyl-2-ethylimidazolium)dibromide; and
dodecyl-bis(1-decyl-2,4,5-trimethylimidazolium) dibromide.

11. A compound having the formula $$\left[ \begin{array}{c} R^3 \quad R^4 \quad R^6 \quad R^7 \\ R^{\diagdown N} \diagup N{-}X{-}N \diagup N{-}R^1 \\ R^2 \qquad R^5 \end{array} \right]^{2+} Y^{2-}$$

wherein

R and $R^1$ are independently $C_{4-20}$-alkyl;

X is $C_{6-18}$-alkylene;

$R^2$ to $R^7$ are independently hydrogen or $C_{1-4}$-alkyl provided that at least one of $R^2$ to $R^4$ and $R^5$ and $R^7$ is $C_{1-4}$-alkyl;

Y is one or more anions providing two negative charges to give a neutral molecule;

with the exception of decyl-bis-(1-decyl-2-methylimidazolium) dibromide.

12. A compound as claimed in claim 11 wherein $R^3$, $R^4$, $R^6$ and $R^7$ are each hydrogen.

13. A compound as claimed in either claim 11 or claim 12 wherein $R^2$ and $R^5$ are both methyl.

14. The compound $$\left[ C_{10}H_{21}{\diagdown}N \diagup N{-}(CH_2)_{12}{-}N \diagup N{-}C_{10}H_{21} \atop CH_3 \qquad CH_3 \right]^{2+} Y^{2-}$$

Wherein Y is as defined in claim 1.

15. A compound having the Formula VIII $$\left[ R{-}N{\diagdown}\underset{R^2}{\diagup}N{\text{---}}\left(X{-}N{\diagdown}\underset{R^5}{\diagup}N\right)_{n}{-}R^1 \right]^{(n+1)+} Y^{(n+1)-} \quad \text{VIII}$$

(with $R^3, R^4$ on first ring and $R^6, R^7$ on repeating ring)

wherein

R to $R^7$, X and Y are as defined in claim 6, and n=2–6.

16. A process for making a compound of formula $$R{-}N{\diagdown}\underset{R^2}{\diagup}N \quad \begin{array}{c} R^3 \quad R^4 \end{array} \quad \text{XI}$$

17. A compound of formula X $$Hal{-}X{-}\underset{(+)}{N}{\diagdown}\underset{R^5}{\diagup}N{-}X{-}Hal \quad Hal^- \quad X$$

(with $R^6, R^7$ on ring)

wherein $R^5$ to $R^7$ are independently hydrogen or $C_{1-4}$-alkyl or $R^6$ and $R^7$ together with the carbon atoms to which they are attached form a phenyl ring;

$X^2$ is a $C_{6-18}$-alkylene; and

Hal is chlorine, bromine or iodine.

18. A method as claimed in claim 1 wherein each of A and B represents an imidazolium group.

19. A method as claimed in claim 1 wherein from 2 to 50 ppm of said salt of Formula I is added to the water.

* * * * *